(12) United States Patent
Barrett

(10) Patent No.: US 6,340,355 B1
(45) Date of Patent: *Jan. 22, 2002

(54) INTRAOCULAR IRRIGATION/ASPIRATION DEVICE

(76) Inventor: Graham David Barrett, 56 Dampier Avenue, City Beach, W.A. 6015 (AU)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/242,749
(22) PCT Filed: Aug. 22, 1997
(86) PCT No.: PCT/AU97/00536
  § 371 Date: Feb. 19, 1999
  § 102(e) Date: Feb. 19, 1999
(87) PCT Pub. No.: WO98/07398
  PCT Pub. Date: Feb. 26, 1998

(30) Foreign Application Priority Data

Aug. 22, 1996 (AU) ............................................. PO1787

(51) Int. Cl.⁷ ................................................. A61M 1/00
(52) U.S. Cl. .............................. 604/27; 604/43; 604/35
(58) Field of Search ............................... 604/27, 43.01, 604/95.01, 95.02, 48, 35, 43, 264, 523

(56) References Cited

U.S. PATENT DOCUMENTS

| | | | | |
|---|---|---|---|---|
| 3,589,363 A | | 6/1971 | Banko | ..................... 128/276 |
| 4,645,493 A | * | 2/1987 | Ferrando et al. | ............. 604/174 |
| 4,963,147 A | * | 10/1990 | Agee et al. | .................. 606/170 |
| 5,169,386 A | * | 12/1992 | Becker et al. | ................. 604/49 |
| 5,547,473 A | * | 8/1996 | Peyman | ....................... 604/27 |
| 5,558,634 A | * | 9/1996 | Mitchell | ....................... 604/35 |
| 5,735,811 A | * | 4/1998 | Brisken | ....................... 604/22 |
| 5,788,680 A | * | 8/1998 | Linder | ....................... 604/280 |
| 5,824,041 A | * | 10/1998 | Lenkar et al. | ................. 623/1 |
| 5,928,218 A | * | 7/1999 | Gelbfish | ..................... 604/540 |

FOREIGN PATENT DOCUMENTS

| | | | | |
|---|---|---|---|---|
| JP | 8-038541 | | 2/1996 | ............ A61F/9/007 |
| WO | WO 94/22402 | | 10/1994 | ............. A61F/9/00 |
| WO | WO 96/07377 | | 3/1996 | ............. A61F/9/00 |
| WO | WO 96/38091 | | 12/1996 | ............ A61B/17/20 |

* cited by examiner

Primary Examiner—Anhtuan T. Nguyen
Assistant Examiner—Ann Lam
(74) Attorney, Agent, or Firm—Fish & Neave; Nicola A. Pisano

(57) ABSTRACT

An intraocular irrigation/aspiration device (10) including a hollow shaft (12) with a distal tip portion (20) and a proximal portion (24). The shaft (12) includes a lumen (18) extending through the shaft (12) wherein the lumen (18) is of reduced cross-sectional area in the proximal portion (24) so as to regulate aspiration of fluid and reduce post occlusion surge phenomena. Preferably, the device (10) includes an outer sleeve (26) which is flexible so as to enable a small incision in the eye to engage closely with the shaft (12).

19 Claims, 7 Drawing Sheets

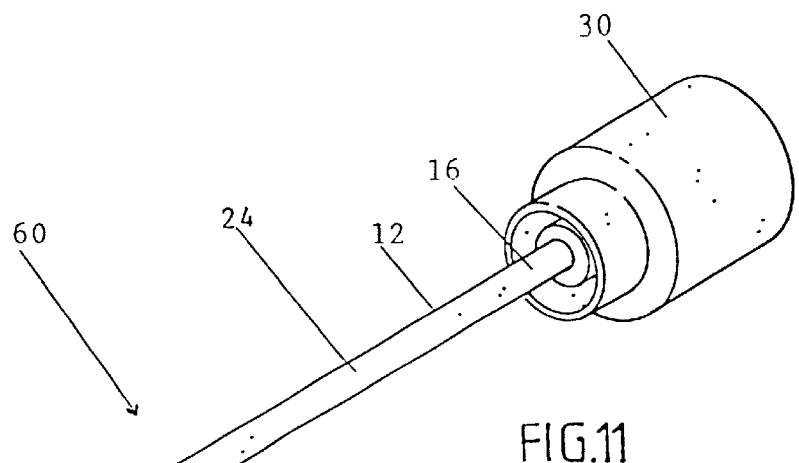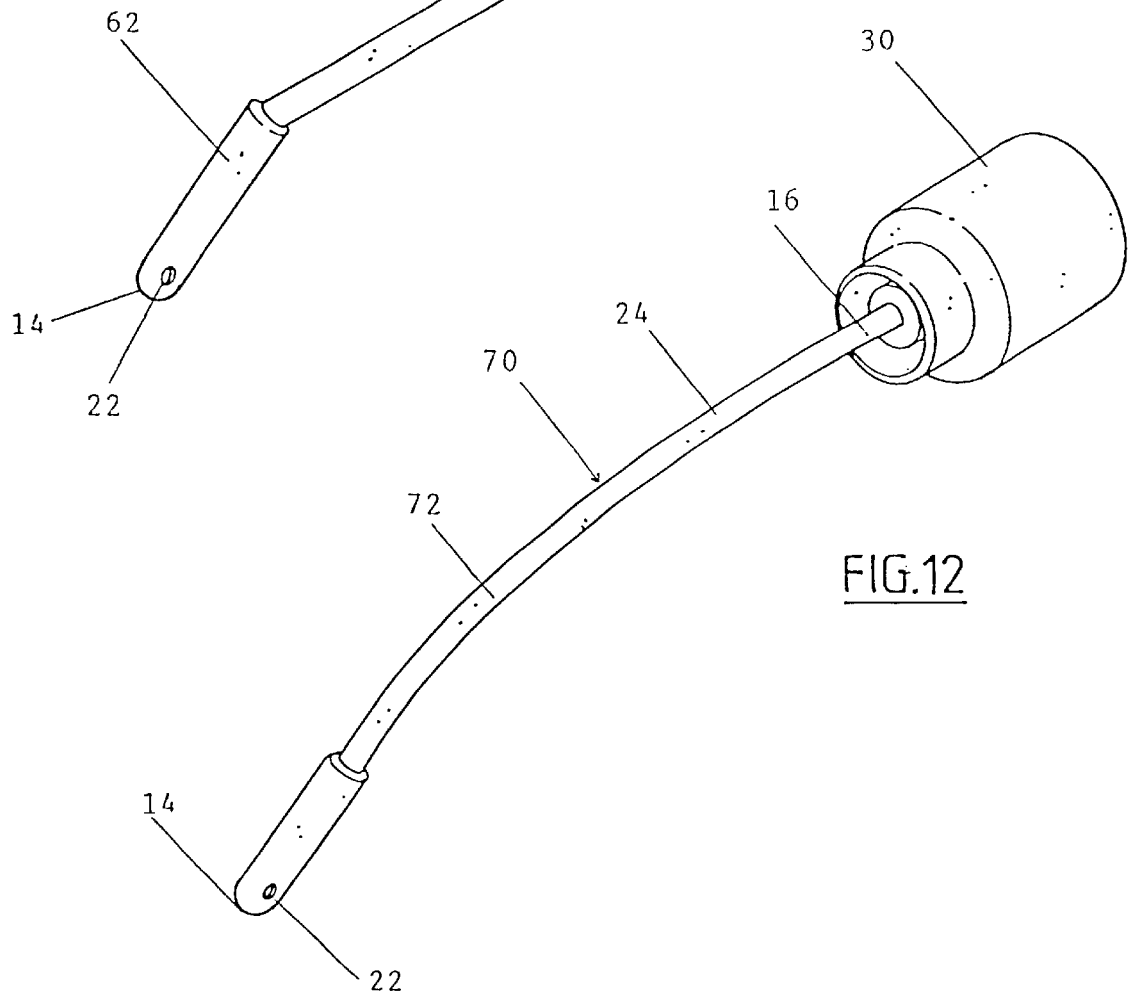

INTRAOCULAR IRRIGATION/ASPIRATION DEVICE

FIELD OF INVENTION

The present invention relates generally to intraocular irrigation/aspiration devices.

BACKGROUND OF THE INVENTION

Occurrence of the disease known as cataracts, in which the lens of the eye becomes clouded, is common, and can lead to blindness. It has become accepted practice to alleviate this condition by surgically removing the cataract-affected lens and replacing it by an artificial intraocular lens.

The cataract-affected lens is usually removed by manual extraction or phaco-emulsification. Manual extraction requires expression of the nucleus of the lens through a wound of about 12 mm in length. The residual peripheral lens material is then removed by an intraocular irrigation/aspiration device.

The technique known as phaco-emulsification, as described, for example, in U.S. Pat. No. 3,589,363, enables removal of the cataract-affected lens through a much smaller incision of about 2.5–4 mm, for example, 3.2 mm. This is accomplished using high frequency ultrasound energy, typically of 40 kHz frequency, that is transmitted by a phaco-emulsification needle to fragment or emulsify the nucleus of the cataract-affected lens. Once fragmented or emulsified, the nuclear material is aspirated through a lumen of the phaco-emulsification needle.

Japanese patent application No. 80-38451 describes a phaco-emulsification tip having a reduced diameter portion proximal of the tip face that reduces the suction flow rate and allows shortening of the overall length of the tip.

WO 94/22402 describes a phaco-emulsification method and tip wherein the tip is configured to enhance generation of shockwaves and/or focussing of shockwaves. Some embodiments of phaco-emulsification tip includes a lumen having a diameter smaller than the diameter of the opening at the distal endface of the tip.

An improved phaco-emulsification needle is also described and claimed in Australian patent application No. 33365/95 (International Patent Application No PCT/AU95/00558), in the name of the present applicant, wherein the needle includes a mid-region portion having a plurality of outwardly extending projections forming longitudinally-oriented grooves. The grooves ensure adequate cooling of the needle in the vicinity of the entry wound, thereby reducing the risk of thermal damage to tissue in the vicinity of the entry wound. Some embodiments of that invention include reduced-diameter portions to accommodate the presence of the longitudinally-oriented grooves.

After the nuclear material of the lens has been aspirated or emulsified by use of the phaco-emulsification needle and aspirated through a lumen thereof, there remains in the eye residual lens material which is derived from softer lens material which originally surrounded the nucleus.

After treatment with the phaco-emulsification needle it is necessary to remove the residual lens material by means of an intraocular irrigation/aspiration device. This device includes a tip which is inserted through the incision in the eye. The tip includes a small opening at its distal end which opening is about 0.3 mm in dimension. A lumen leads from the opening through the device to an aspiration device. Further, the device includes an outer sleeve which extends to a point adjacent to the tip to form an external conduit which is connected to a supply of fluid.

There is no need to apply energy to the intraocular irrigation/aspiration device as the lens nucleus has already been fragmented or emulsified during phaco-emulsification. The device is connected to an aspirator which applies suction to the lumen and hence to the opening at the tip. In this way residual lens material is drawn through the opening and then along the lumen so as to remove the residual lens material from the interior of the eye. Simultaneously, fluid is fed through the external conduit to the interior of the eye to replace the aspirated fluid and maintain the volume of fluid and pressure within the chamber of the eye.

In operation of the intraocular irrigation/aspiration device, it is important to ensure that there is a balance between infusion and aspiration of fluids so as to maintain stable pressure and volume within the intraocular chambers. This reduces the likelihood of inadvertent aspiration of structures such as the iris, or the delicate posterior capsule which divides the eye into anterior and posterior chambers. The posterior capsule is liable to rupture if engaged by the aspiration port which may result in loss of the vitreous gel which fills the posterior chamber of the eye. An intact capsule is also important to support a posterior chamber intraocular lens implant, and therefore inadvertent rupture of the posterior capsule is a serious complication which may result in an unsatisfactory technical result and a poor visual outcome from cataract surgery. It has been found that the distal opening or port of the tip of the aspiration device sometimes becomes transiently blocked or occluded during aspiration such as by a relatively large piece of residual lens material. This leads to a temporary increase in vacuum within the lumen which is relieved when the blocking material is eventually drawn through the opening with equalisation of pressure within the chamber of the eye and the aspiration device. However, this equalisation of pressure can induce a surge of fluid along the lumen and a transient reduction in pressure and volume within the pressure of the eye or chamber instability. It is important that adequate infusion of fluid is available to counteract the reduction in pressure and volume.

An outer sleeve of the irrigation/aspiration device may be formed from rigid plastic or metal which resist deformation by the incision. A rigid sleeve however, increases leakage from the wound reducing pressure within the eye, and the ability to maintain a stable chamber volume of fluid. A soft outer sleeve is better able to seal the incision and reduce wound leakage. A tight sealed incision however, may compress a soft sleeve and reduce the flow and infusion of the irrigating fluid into the eye which is necessary to replace aspirated fluid and maintain a stable chamber with respect to pressure and volume.

SUMMARY OF THE INVENTION

The present invention provides an intraocular irrigation/aspiration device in which the aspiration of fluid and lens material is regulated and the post occlusion surge phenomenon is reduced.

In accordance with one aspect of the present invention there is provided an intraocular irrigation/aspiration device including a hollow shaft having first and second ends, a tip at the first end of the shaft, said tip including an opening and a lumen extending from the opening to the second end of the shaft, wherein the lumen has a portion of reduced internal cross-sectional area over at least part of its length.

BRIEF DESCRIPTION OF THE DRAWINGS

The present invention will now be described, by way of example, with reference to the accompanying drawings, in which:

FIG. 11 is a side elevation of a modified form of device in accordance with the present invention including a bent distal portion; and FIG. 12 is a side elevation of a modified form of device in accordance with the present invention including a curved shaft.

DETAILED DESCRIPTION OF THE PREFERRED EMBODIMENTS

Figure 1:
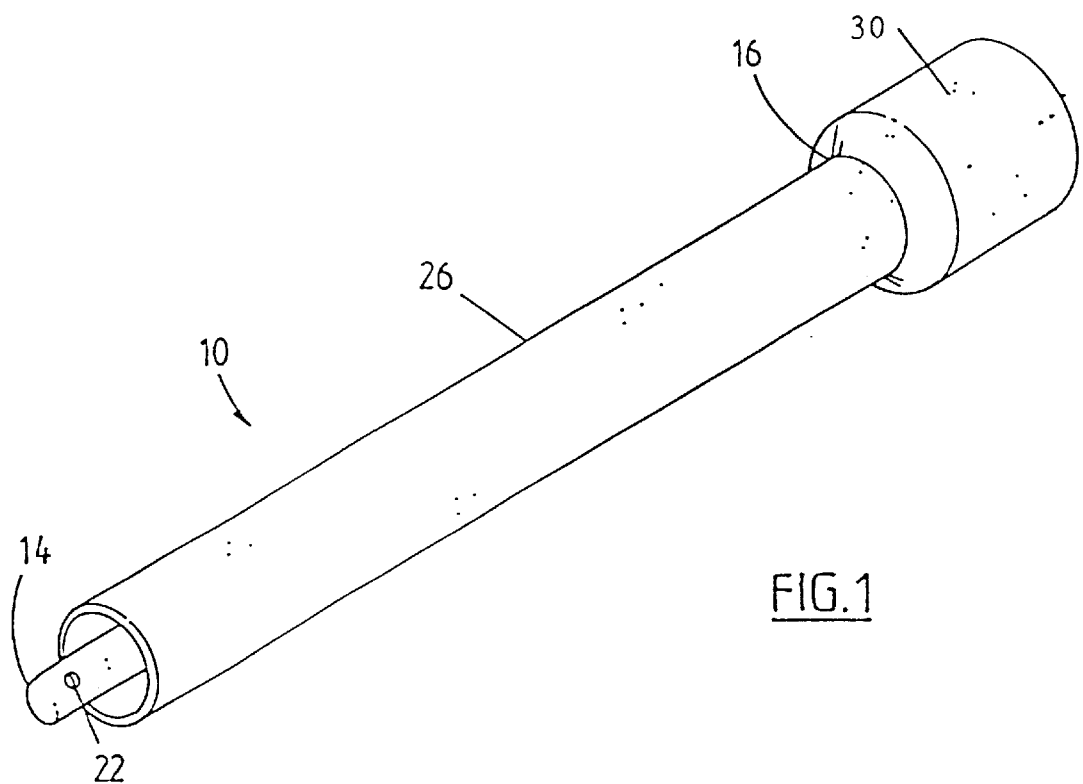
FIG. 1 is perspective view of a first embodiment of intraocular irrigation/aspiration device according to the present invention.
Figure 2:
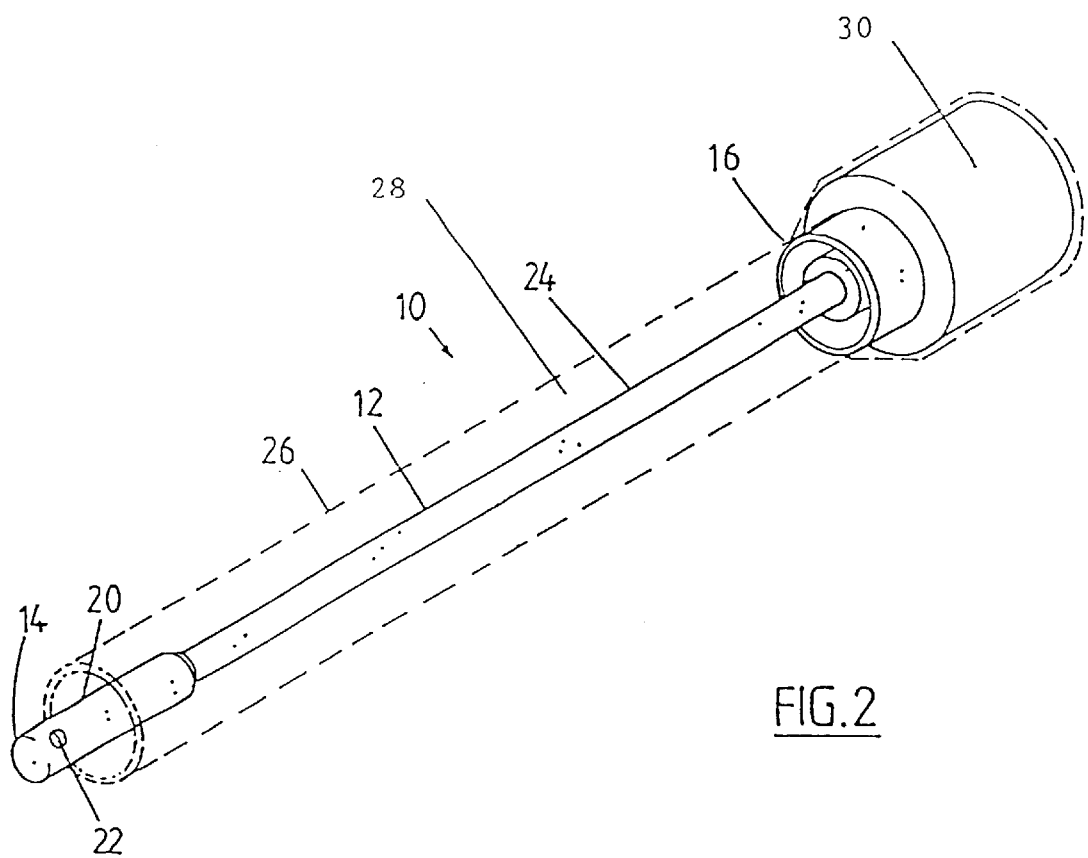
FIG. 2 is a view similar to FIG. 1 with an outer sleeve shown in phantom.
Figure 3:
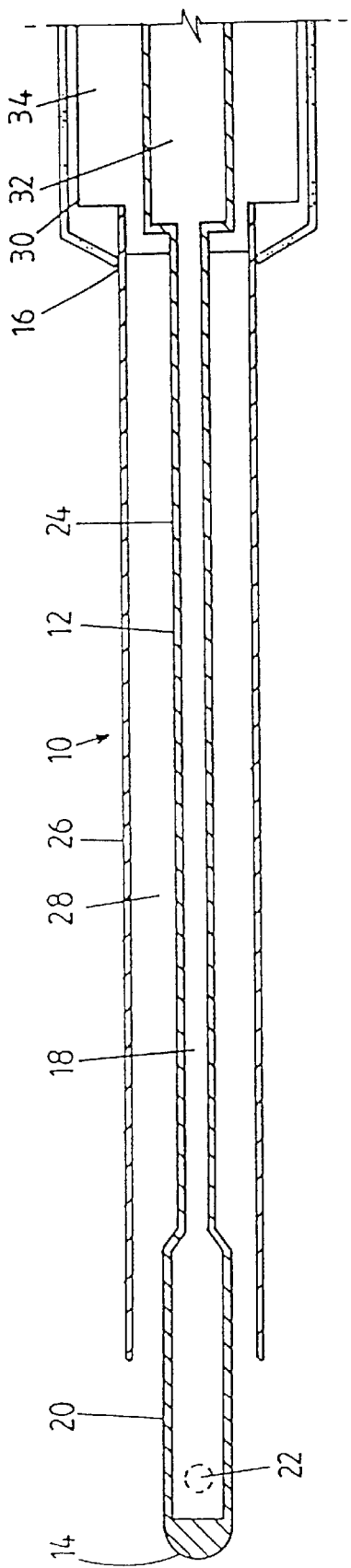
FIG. 3 is a longitudinal section through the device of FIGS. 1 and 2.

In FIGS. 1 to 3, there is shown an intraocular irrigation/aspiration device 10 in accordance with the present invention.

The device 10 includes a shaft 12 having a first or distal end 14 and a second or proximal end 16. The shaft 12 is hollow and includes a lumen 18 extending from the distal end 14 to the proximal end 16. At the distal end 14 there is provided a distal tip portion 20 which includes an opening 22. Adjacent the tip portion 20 there is provided a mid-region portion 24 of reduced external and internal dimension.

The shaft 12 is typically formed of metal. Extending around the shaft 12 is an annular external sleeve 26. The sleeve 26 is formed of any suitable material which may be elastomeric material or metal. Elastomeric material is far more flexible than metal and is therefore preferred for most applications. The sleeve 26 and the shaft 12 define an annular external passageway or conduit 28 extending between the first and second ends 14 and 16.

The opening 22 is typically about 0.3 mm in lateral dimension. Further, the shaft 12 at the distal tip portion 20 is typically of the order of 0.6 to 1.0 mm in internal cross sectional dimension such as about 0.8 mm in internal cross sectional dimension. The shaft 12 at the mid-region portion 24 is of lesser internal dimension than the distal portion and is typically of the order of 0.1 to 0.5 mm in internal cross sectional dimension such as about 0.3 mm.

Further, the shaft 12 at the tip portion 20 is typically of the order of 0.8 to 1.2 mm in external cross sectional dimension such as about 1.00 mm in external cross sectional dimension. The mid-region portion 24 is typically about 0.4 to 0.8 mm in external cross sectional dimension such as about 0.6 mm. The shaft 12 may have a wall thickness of about 0.1 mm.

The sleeve 26 may have an internal cross-sectional dimension of about 1.5 to 3 mm such as about 2 mm.

In use, the device 10 is inserted through an incision in an eye such that the distal tip portion 20 is located within the eye and the wall of the eye is in engagement with the outer sleeve 26 at a point corresponding with the proximal portion 24. Fluid is infused into the eye through the annular passageway 28 and simultaneously fluid and residual lens material is aspirated through the opening 22 and the lumen 18. The presence of the mid-region portion 24 of the lumen 18 with reduced internal diameter means that if there is a temporary blockage or occlusion of the opening 22, which is then released suddenly, the surge of fluid along the lumen 18 is constrained by the reduced diameter of the proximal portion compared to the distal portion. This reduces fluctuations in volume and pressure in the intraocular chambers of the eye.

The narrower proximal lumen also increases the resistance to aspirational flow whilst maintaining the size of the aspiration port 22, at approximately 0.3 mm. The device therefore favourably regulates aspirational flow.

Reducing the size of the aspiration port to less than 0.3 mm would increase the resistance to aspiration flow, but would compromise the efficiency of removal of soft lens material as only smaller fragments could be engaged by the aspiration port. Furthermore, simply reducing the size of the aspiration port to less than 0.3 mm would not diminish the post occlusion surge phenomena described previously.

Further, as can be seen in FIG. 3 especially the device 10 is connected to a handle 30. The handle 30 contains a first conduit 32 which is connected in use to an aspirator (not shown) and a second conduit 34 which is connected in use to a supply of fluid (not shown). The conduit 32 is connected to the lumen 18 and the conduit 34 is connected to the passageway 28. The handle 30 may be formed separately from the device 10 or it may be formed integrally therewith.

Also, the reduced external cross-sectional dimension of the mid-region portion 24, especially in the case where the sleeve 26 is formed of elastomeric or other flexible material, enables a small incision in the eye to engage closely with the shaft 12. This reduces wound leakage, but also increases the infusion of fluid compared with a conventional intraocular irrigation/aspiration device. The device also enhances the flow of infusion fluid necessary to compensate for fluctuations in chamber pressure and volume caused by aspiration. The balance between infusion and aspiration is therefore enhanced which increases the stability of the chamber and improves the safety of the cataract procedure. The irrigation/aspiration device therefore helps regulate aspirational flow, and reduces the post occlusion surge phenomena, but also improves the infusion of irrigating fluid available to respond to reductions in chamber volume and pressure.

The balance between the outflow of fluid from the eye due to aspiration and wound leakage, and the inflow of fluid due to irrigation, is favourably influenced by the design of the irrigation/aspiration device resulting in a deeper more stable pressurised anterior chamber enhancing the safety of this phase of the cataract procedure.

Figure 4:
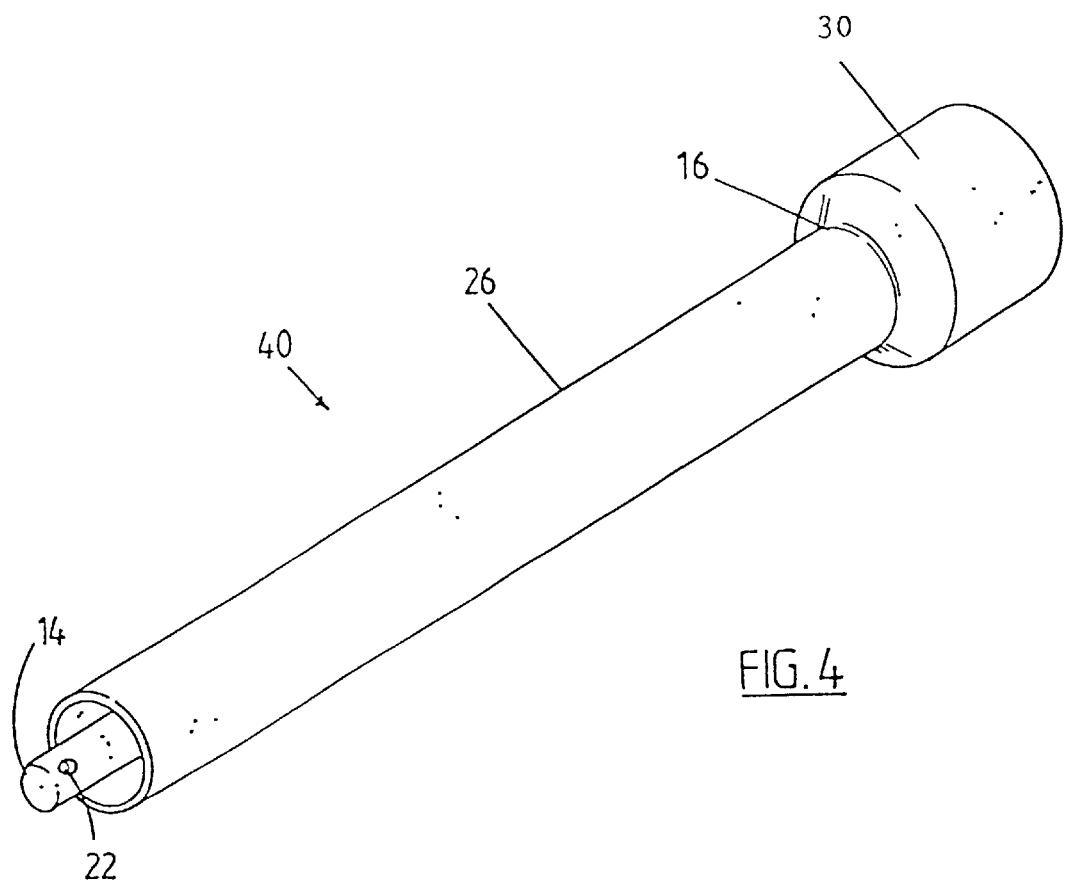
FIG. 4 is a perspective view of a second embodiment of intraocular irrigation/aspiration device according to the present invention.
Figure 5:
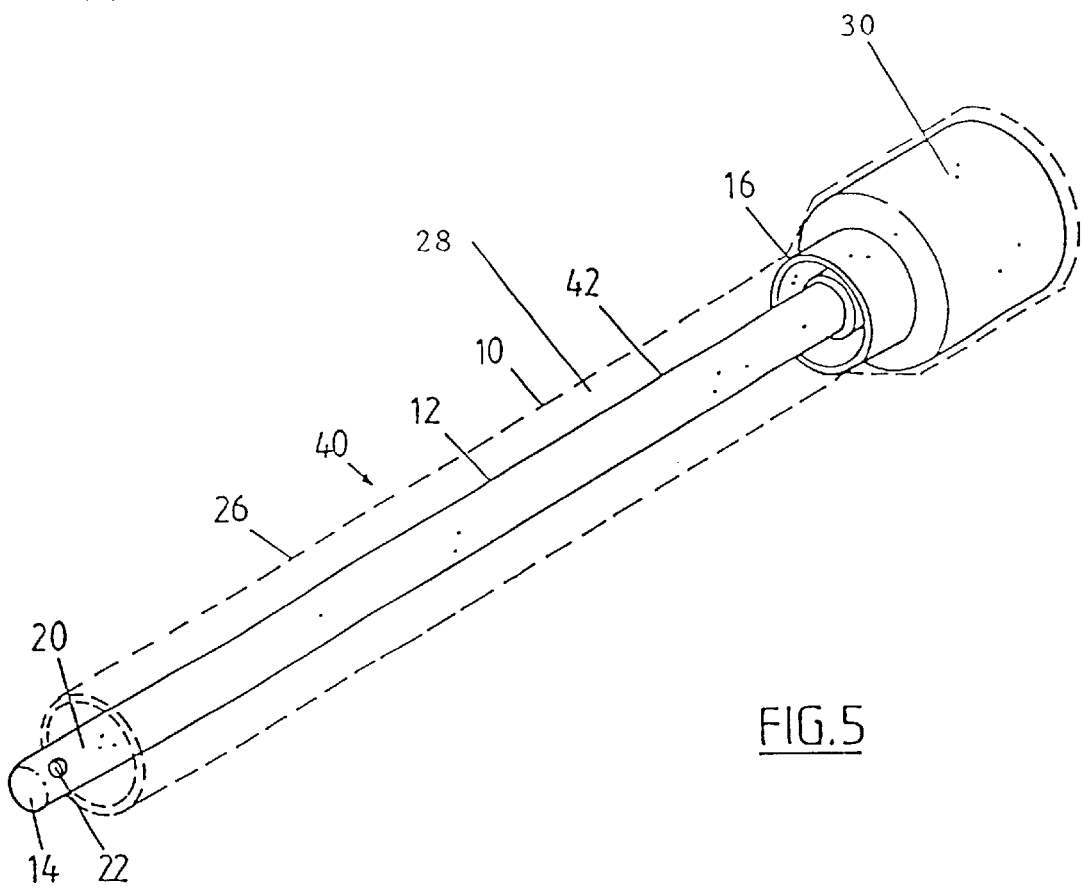
FIG. 5 is a view similar to FIG. 4 with an outer sleeve shown in phantom.
Figure 6:
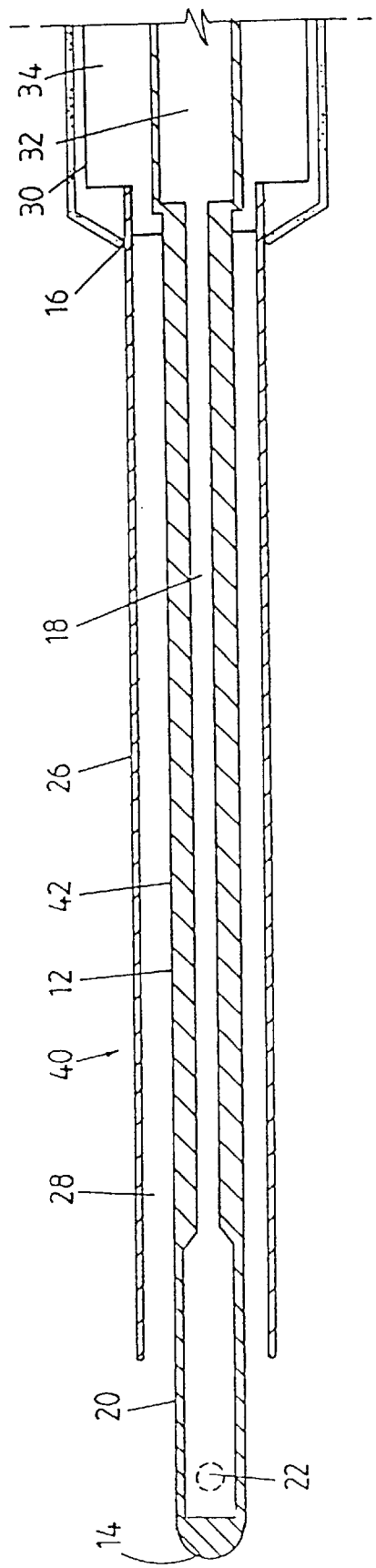
FIG. 6 is a longitudinal section through the device of FIGS. 4 and 5.

In FIGS. 4 to 6 there is shown a second embodiment of an intraocular irrigation/aspiration device 40 in accordance with the present invention. The embodiment of FIGS. 4 to 6 is similar to that of FIGS. 1 to 3 and like reference numerals denote like parts.

Further, in the second embodiment the mid-region portion of lumen 18 is of reduced internal cross-sectional dimension compared to the distal portion as in the first embodiment.

However, the external cross-sectional dimension of the proximal portion 42 of the shaft 12 is substantially the same as the external cross-sectional dimension of the distal portion. Thus, the shaft 12 has substantially the same external cross-sectional dimension throughout as best seen in FIG. 6.

In the second embodiment the advantage of reduction of surge of pressure after occlusion and the regulation of aspiration is still obtained as with the first embodiment but the ability to operate with a small incision in the eye with improved infusion of fluid compared with conventional devices is not achieved.

In FIGS. 7 to 10 there is shown a third embodiment of an intraocular irrigation/aspiration device 50 in accordance with the present invention. The embodiment of FIGS. 7 to 10 is similar to that of FIGS. 1 to 3 and like reference numerals denote like parts.

Figure 10:
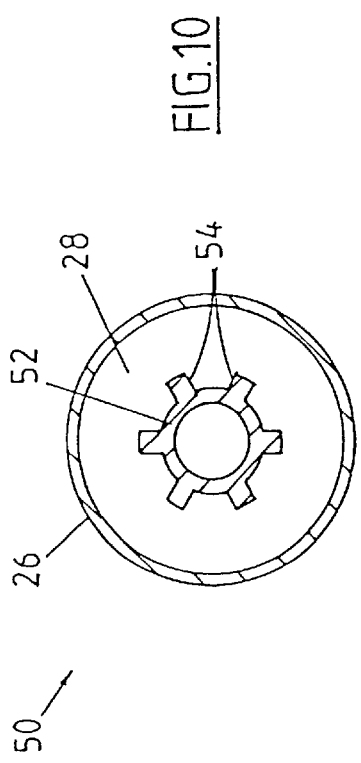
FIG. 10 is a transverse section along the line 10—10 of FIG. 9.

In the third embodiment shown in FIGS. 7 to 10 a mid-region portion 52 of the shaft 12 has reduced internal and external cross-sectional dimensions as in FIGS. 1 to 3. However, the mid-region portion 52 also has a plurality of outwardly extending spaced external projections 54 as best seen in FIG. 10. As shown, the projections 54 are preferably in the form of longitudinally extending ribs. The projections 54 ensure that the sleeve 26 even when formed of elastomeric or other flexible material is not pushed firmly into engagement with the shaft 12 by the wall of the eye. This ensures that there is always a clear path for infusion liquid to pass to the interior of the eye along the passageway 28.

Figure 7:
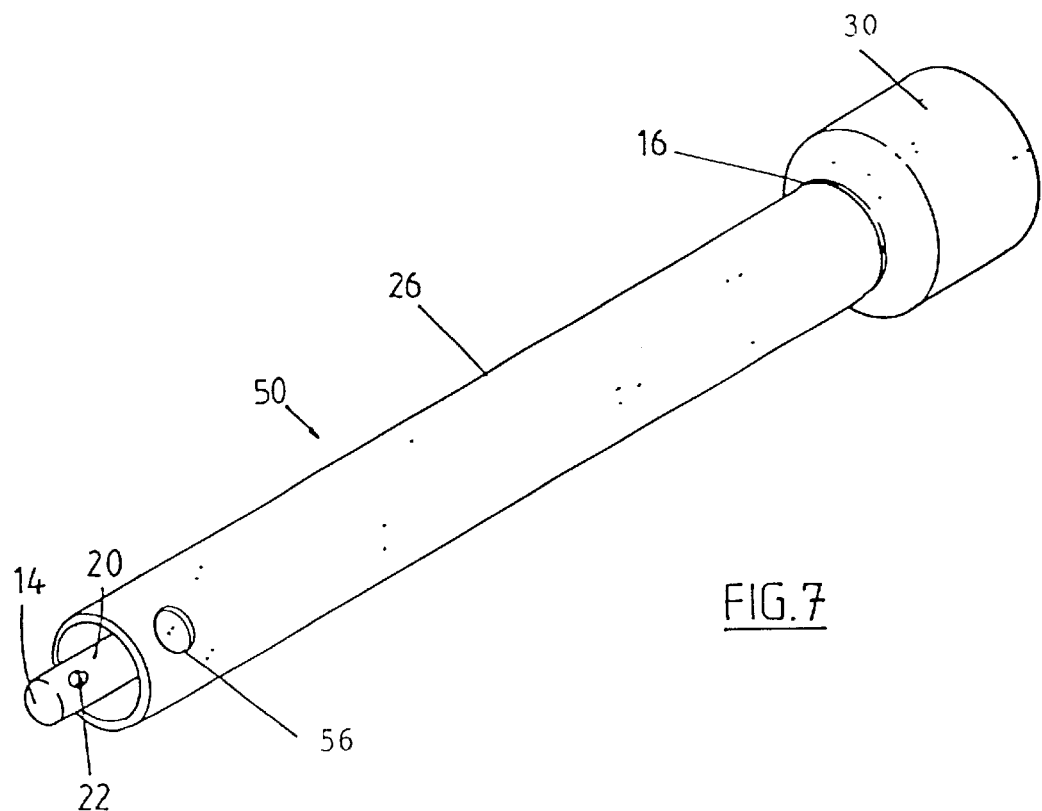
FIG. 7 is a perspective view of a third embodiment of intraocular irrigation/aspiration device according to the present invention.
Figure 8:
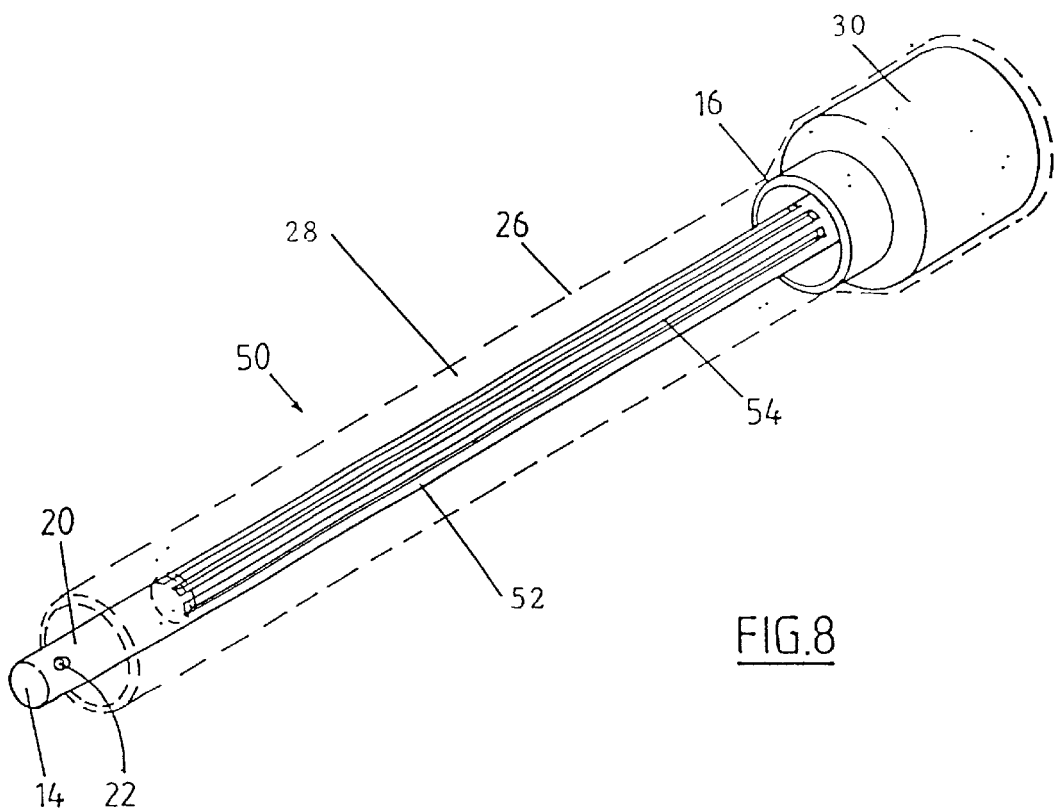
FIG. 8 is a view similar to FIG. 7 with an outer sleeve shown in phantom.
Figure 9:
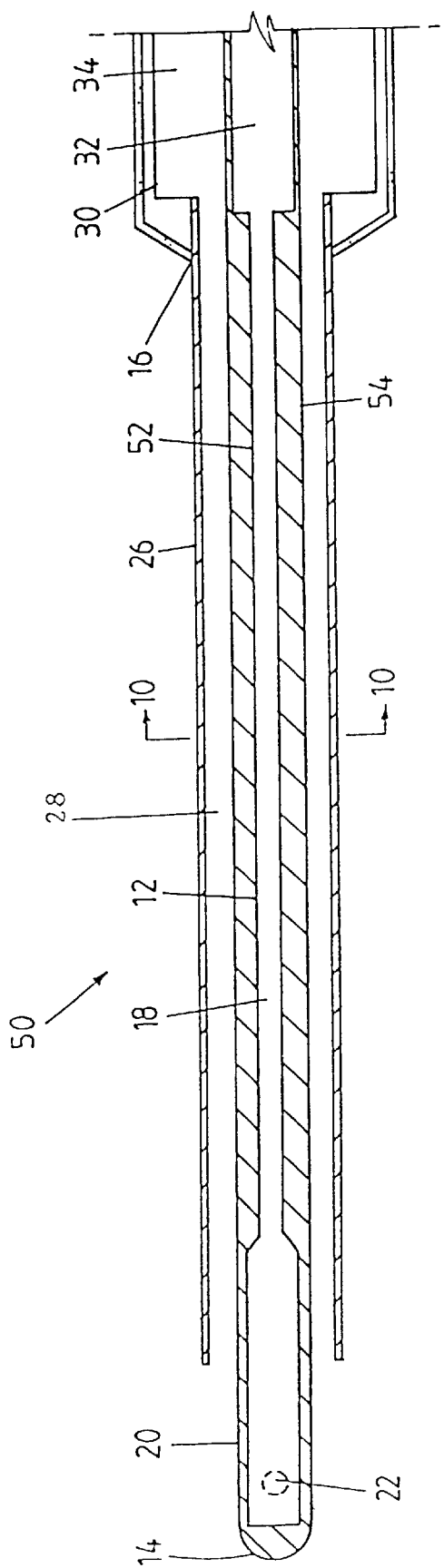
FIG. 9 is a longitudinal section through the device of FIGS. 7 and 8.

Further, as can be seen in FIG. 7, the sleeve 26 may have at least one opening 56 adjacent a distal end thereof for escape of irrigating fluid. Preferably, there are two opposed openings 56, one on either side, for this purpose. Openings equivalent to the openings 56 may also be found in the first and second embodiments of the present invention described hereinabove.

In FIG. 11, there is shown an intraocular irrigation/aspiration device 60 in accordance with the present invention (with the sleeve 26 absent for greater clarity) in which the distal portion 62 is bent compared to the remainder of the shaft 12, that is, the distal portion 62 is inclined at an angle to the remainder of the shaft 12. In the embodiments of FIGS. 1 to 10 the distal portion 20 is aligned with the remainder of the shaft 12.

In FIG. 12 there is shown an intraocular irrigation/aspiration device 70 in accordance with the present invention which includes a curved shaft 72 whereas in the embodiments of FIGS. 1 to 10 the shaft 12 is straight.

The various components such as the shaft 12 and the annular sleeve 26 in the device of the present invention are preferably circular in shape in which case the cross-sectional dimensions referred to hereabove may be referred to as cross-sectional diameters. However, it is to be understood that the various components of the device of the present invention may have other cross-sectional shapes.

Modifications and variations such as would be apparent to a skilled addressee are deemed within the scope of the present invention.

What is claimed is:

1. An intraocular irrigation/aspiration device for aspirating emulsified material from an intraocular cavity, the device comprising:

a sleeve having proximal and distal ends, the proximal end adapted to be coupled to an irrigation source; and a rigid shaft disposed concentrically in the sleeve and spaced apart from the sleeve to define an annular irrigation channel, the shaft having proximal and distal ends, and a lateral surface, the proximal end adapted to be coupled to a suction source, the distal end of the shaft disposed in fixed relation extending beyond the distal end of the sleeve and comprising a tip including an opening in the lateral surface having a pre-selected size, a lumen extending from the opening to the proximal end, the lumen having a first portion defining a chamber with a first cross-sectional area that communicates with the opening, and a second portion with a second cross-sectional area disposed between the chamber and the proximal end, the second cross-sectional area being smaller than the first cross-sectional area, wherein the first and second cross-sectional areas and pre-selected size of the opening are selected to control pressure fluctuations in the intraocular cavity arising from post-occlusion surge events.

2. An intraocular irrigation/aspiration device according to claim 1, wherein the shaft includes a distal tip portion and a mid-region portion, the distal tip portion containing the tip and the first portion of the lumen having the first cross-sectional area that defines the chamber, the mid-region portion containing the second portion of the lumen having the second cross-sectional area.

3. An intraocular irrigation/aspiration device according to claim 1, wherein the first cross-sectional area has a dimension in a range from about 0.6 to 1.00 mm.

4. An intraocular irrigation/aspiration device according to claim 1, wherein the second cross-sectional area has a dimension in a range from about 0.1 to 0.5 mm.

5. An intraocular irrigation/aspiration device according to claim 2, wherein the mid-region portion has an external cross-sectional dimension smaller than an external cross-sectional dimension of the distal tip portion.

6. An intraocular irrigation/aspiration device according to claim 5, wherein the external cross-sectional dimension of the distal tip portion is in a range from about 0.8 to 1.2 mm.

7. An intraocular irrigation/aspiration device according to claim 5, wherein the external cross-sectional dimension of the mid-region portion is in a range from about 0.4 to 0.8 mm.

8. An intraocular irrigation/aspiration device according to claim 2, wherein an external cross-sectional dimension of the mid-region portion is substantially equal to an external cross-sectional dimension of the distal tip portion.

9. An intraocular irrigation/aspiration device according to claim 8, wherein the distal tip portion and the mid-region portion have external cross-sectional dimensions in a range from about 0.8 to 1.2 mm.

10. An intraocular irrigation/aspiration device according to claim 2, wherein the mid-region portion has an external cross-sectional dimension smaller than an external cross-sectional dimension of the distal tip portion, and the mid-region portion has a plurality of outwardly extending spaced external projections adapted to maintain a path for infusion of liquid.

11. An intraocular irrigation/aspiration device according to claim 10, wherein the projections define longitudinally extending ribs.

12. An intraocular irrigation/aspiration device according to claim 1, wherein the sleeve is flexible.

13. An intraocular irrigation/aspiration device according to claim 12, wherein the sleeve comprises elastomeric material.

14. An intraocular irrigation/aspiration device according to claim 1, wherein the sleeve has at least one opening adjacent the distal end thereof for escape of irrigating fluid.

15. An intraocular irrigation/aspiration device according to claim 1, wherein the sleeve has an internal cross-sectional dimension in a range from about 1.5 to 3.0 mm.

16. An intraocular irrigation/aspiration device according to claim 1, wherein an interior surface of the sleeve and the lateral surface of the shaft define the annular irritation channel, the channel extending between the proximal and distal ends of the shaft.

17. An intraocular irrigation/aspiration device according to claim 16, wherein the device is adapted to be connected to a handle containing a first conduit adapted to be connected to the suction source and a second conduit adapted to be connected to the irrigation source, the first conduit adapted to be connected to the lumen and the second conduit adapted to be connected to the annular irrigation channel.

18. An intraocular irrigation/aspiration device according to claim 2, wherein the distal tip portion has a first longitudinal axis and the mid-region portion has a second longitudinal axis, and the first and second longitudinal axes are not collinear.

19. An intraocular irrigation/aspiration device according to claim 1, wherein the opening has a dimension of at least 0.3 mm.

* * * * *